US006987213B2

(12) United States Patent
Kumagai et al.

(10) Patent No.: US 6,987,213 B2
(45) Date of Patent: *Jan. 17, 2006

(54) METHOD FOR CONFERRING HERBICIDE, PEST, OR DISEASE RESISTANCE IN PLANT HOSTS

(75) Inventors: Monto H. Kumagai, Davis, CA (US); Guy R. della-Cioppa, Vacaville, CA (US)

(73) Assignee: Large Scale Biology Corporation, Vacaville, CA (US)

(*) Notice: Subject to any disclaimer, the term of this patent is extended or adjusted under 35 U.S.C. 154(b) by 291 days.

This patent is subject to a terminal disclaimer.

(21) Appl. No.: 09/969,447

(22) Filed: Oct. 1, 2001

(65) Prior Publication Data

US 2002/0069429 A1    Jun. 6, 2002

Related U.S. Application Data

(63) Continuation of application No. 09/359,302, filed on Jul. 21, 1999, now Pat. No. 6,303,848, which is a continuation-in-part of application No. 09/232,170, filed on Jan. 15, 1999, now abandoned, which is a continuation-in-part of application No. 09/008,186, filed on Jan. 16, 1998, now abandoned.

(51) Int. Cl.
*C12N 15/82* (2006.01)
*C12N 15/83* (2006.01)
*C12N 15/87* (2006.01)

(52) U.S. Cl. .................. 800/280; 800/279; 800/288
(58) Field of Classification Search ................. 800/278, 800/279, 288, 280
See application file for complete search history.

(56) References Cited

U.S. PATENT DOCUMENTS

| | | | |
|---|---|---|---|
| 4,885,248 A | 12/1989 | Ahlquist | 435/468 |
| 5,173,410 A | 12/1992 | Ahlquist | 435/91.1 |
| 5,312,910 A | 5/1994 | Kishore et al. | 536/23.2 |
| 5,316,931 A | 5/1994 | Donson et al. | 435/468 |
| 5,466,788 A | 11/1995 | Ahlquist et al. | 536/24.1 |
| 5,491,076 A | 2/1996 | Carrington et al. | 435/70.1 |
| 5,500,360 A | 3/1996 | Ahlquist et al. | 435/468 |
| 5,589,367 A | 12/1996 | Donson et al. | 435/468 |
| 5,602,242 A | 2/1997 | Ahlquist et al. | 536/23.72 |
| 5,627,060 A | 5/1997 | Ahlquist et al. | 435/468 |
| 5,773,701 A | 6/1998 | Braun et al. | 800/278 |
| 5,811,653 A | 9/1998 | Turpen | 800/278 |
| 5,866,785 A | 2/1999 | Donson et al. | 800/278 |
| 5,889,190 A | 3/1999 | Donson et al. | 800/288 |

FOREIGN PATENT DOCUMENTS

WO    WO 98/59046    12/1998

OTHER PUBLICATIONS

Hayes, et al., "Agroinfection of *Triticum aestivum* with Cloned DNA of Wheat Dwarf Virus," *J. Gen. Virol.* 69:891-896 (1988).
Kurisu, et al., "Biochemical Characterization of Cucumber Green Mottle Mosaic Virus Ribonucleic Acid," *Virology* 70:214-216 (1976).
Lazarowitz, S., "Infectivity and complete nucleotide sequence of the genome of a South African isolate of maize streak virus," *Nucl. Acids Res.* 16(1):229-249 (1988).
Lebeurier, et al., "Inside-out model for self-assembly of tobacco mosaic virus," *Proc. Natl. Acad. Sci. USA* 74:149-153 (1977).
Lin, et al., *Proc. Natl. Acad. Sci. USA* 96:6535-6540 (1999).
Matthews, *Plant Virology*, 3rd Ed. Academic Press, San Diego (1991).
Meshi, et al., "Nucleotide Sequence of the Coat Protein Cistron and the 3' Noncoding Region of Cucumber Green Mottle Mosaic Virus (Watermelon Strain) RNA," *Virology* 127:54-64 (1983).
*Methods in Enzymol* vols. 68, 100, 101, 118, and 152-155) (1979, 1983, 1986 and 1987).
Miller, W. and Hall, T., "RNA-Dependent RNA Polyerase Isolated from Cowpea Chlorotic Mottle Virus-Infected Cowpeas Is Specific for Bromoviral RNA," *Virology* 132:53-60 (1984).
Misawa, et al., "Expression of an *Erwinia* phytoene desaturase gene not only confers multiple resistance to herbicides interfering with carotenoid biosynthesis but also alters xanthophyll metabolism in transgenic plants," *Plant J.* 6(4):481-489 (1994).
Nagar, et al., "A Geminivirus Induces Expression of a Host DNA Synthesis Protein in Terminally Differentiated Plant Cells," *The Plant Cell*, 7:705-719 (1995).
Nozu, et al., "Chemical and Immunological Characterization of Cucumber Green Mottle Mosaic Virus (Watermelon Strain Protein)," *Virology* 45:577-585 (1971).
*Plant Virology Protocol: From Virus Isolation to Transgenic Resistance* in Methods in Molecular Biology, vol. 81, Foster and Taylor, Ed., Humana Press (1998).
Sambrook, et al., *Molecular Cloning: A Laboratory Manual*, Second Edition, Cold Spring Harbor Labortory Press, Plainview, NY (1982, 1989).

(Continued)

*Primary Examiner*—Ashwin Mehta
(74) *Attorney, Agent, or Firm*—Swanson & Bratschun, L.L.C.

(57) ABSTRACT

The present invention relates to a method for conferring herbicide, pest, and disease resistance in plant hosts. Specifically, the present invention employs transient viral expression vectors to express proteins or enzymes conferring resistance in plant hosts. In addition, a library of nucleotide sequence variants in a sense or antisene orientation may be used to determine the targets of an herbicide or pathogen and to screen suitable viral nucleic acids for herbicide, pest, and disease resistance.

7 Claims, 7 Drawing Sheets

OTHER PUBLICATIONS

Turpen, et al., "Transfection of whole plants from wounds inoculated with *Agrobacteriium tumefaciens* containing cDNA of tobacco mosiac virus," *J. Virol. Methods 42:*227-240 (1993).

Walkey, *Applied Plant Virology,* Chapman & Hall (1991).

Ahlquist, et al., "Complete Nucleotide Sequence of Brome Mosaic Virus RNA3," *J. Mol. Biol. 153:*23-38 (1981).

Armstrong, et al., "Conserved enzymes mediate the early reactions of carotenoids biosynthesis in nonphotosynthetic and photosynthetic prokaryotes," *Proc. Natl. Acad. Sci. USA 87:*9975-9979 (1990).

Armstrong, et al., "Genetic and Biochemical Characterization of Carotenoid Biosynthesis Mutants of *Rhodobacter capsulatus,*" J. *Biol. Chem. 265:*8329-8338 (1990).

Ausubel, F., et al., *Current Protocols in Molecular Biology,* Green Publishing and Wiley-Interscience,NY (1987).

Dawson, et al., "cDNA cloning of the complete genome of tobacco mosaic virus and production of infectious transcripts," *Proc. Natl. Acad. Sci. USA 83:*1832-1836 (1986).

Della-Cioppa, et al., "Genetic Engineering of Herbicide resistance in plants," *Frontiers of Chemistry: Biotechnology,* Chemical Abstract Service, ACS, Columbus, OH, pp. 665-670 (1989).

Deom, et al., "The 30-Kilodalton Gene Prodcut of Tobacco Mosaic Virus Potentiates Virus Movement," *Science 237:* 389-394 (1987).

Dijkstra, et al., *Practical Plant Virology: Protocols and Exercises,* Springer Verlag (1998).

*DNA Cloning,* D.M. Clover, Ed., IRL Press, Oxford (1985).

Donson, et al., " *Agrobacterium*-Mediated Infectivity of Cloned Digitaria Streak Virus DNA," *Virology 162:*248-250 (1988).

Elmer, et al., "*Agrobacterium*-mediated inoculation of plants with tomato golden mosaic virus DNAs," *Plant Mol. Biol. 10:*225-234 (1988).

Fukuda, et al., "The Site of Initiation of Rod Assembly on the RNA of a Tomato and a Cowpea Strain of Tobacco Mosaic Virus," *Virology 101:*493-502 (1980) .

Gardiner, et al., "Genetic analysis of tomato golden mosaic virus: the coat protein is not required for systemic spread of symptom development," *EMBO J. 7*(4):899-904 (1988).

Gardner, et al., "Potato spindle tuber viroid infections mediated by the Ti plasmid of *Agrobacterium tumefaciens,*" *Plant. Mol. Biol.6:*221-228. (1986).

Grimsley, et al., "Agroinfection," an alternative route for viral infection of plants by using the Ti plasmid, *Proc. Natl. Acad. Sci. USA 83:*3282-3286 (1986).

Grimsley, et al.,"*Agrobacterium*-mediated delivery of infectious maize streak virus into maize plants,", Nature, vol. 325, pp. 177-179 (1997).

U.S. Appl. No. 09/359,301, filed Jul. 21, 1999, Kumagai et al.

U.S. Appl. No. 09/359,305, filed Jul. 21, 1999, Kumagai et al.

SEQUENCE LISTING

```
<160> NUMBER OF SEQ ID NOS: 4

<210> SEQ ID NO 1
<211> LENGTH: 32
<212> TYPE: DNA
<213> ORGANISM: Erwinia herbicola

<400> SEQUENCE: 1
gacagaagct ttgcagcatg caaaaaaccg tt                                  32

<210> SEQ ID NO 2
<211> LENGTH: 36
<212> TYPE: DNA
<213> ORGANISM: Erwinia herbicola

<400> SEQUENCE: 2 cccccgcgg tcattgcaga tcctcaatca tcaggc                              36

<210> SEQ ID NO 3
<211> LENGTH: 14
<212> TYPE: DNA
<213> ORGANISM: Arabidopsis thaliana

<400> SEQUENCE: 3
tcgagcggcc gcat                                                     14

<210> SEQ ID NO 4
<211> LENGTH: 8
<212> TYPE: DNA
<213> ORGANISM: Arabidopsis thaliana
```

```
<400> SEQUENCE: 4 gcggccgc                                                                  8
```

METHOD FOR CONFERRING HERBICIDE, PEST, OR DISEASE RESISTANCE IN PLANT HOSTS

This application is a continuation of U.S. application Ser. No. 09/359,302, filed Jul. 21, 1999, now U.S. Pat. No. 6,303,848, which is a continuation-in-part application of U.S. application Ser. No. 09/232,170, filed Jan. 15, 1999, now abandoned, which is a continuation-in-part of U.S. application Ser. No. 09/008,186, filed Jan. 16, 1998, now abandoned.

FIELD OF THE INVENTION

The present invention relates generally to the field of molecular biology and viral genetics. Specifically, the present invention relates to methods for conferring herbicide, pest, or disease resistance in plant hosts.

BACKGROUND OF THE INVENTION

Major areas targeted for genetic improvement in plants include herbicide, insect, and disease resistance. Herbicide resistance can be obtained by genetically engineering plants to respond to toxic chemicals. Many herbicides act by inhibiting a key plant enzyme or protein necessary for growth. For example, the herbicide glyphosate destroys plants by inhibiting the activity of an enzyme necessary for synthesizing aromatic amino acids. Some bacteria contain enzymes that confer resistance to herbicides. A gene encoding a herbicide resistant enzyme from bacteria may be cloned, modified for expression in plants, and inserted crop plant genomes. When sprayed with such herbicide, plants containing the bacterial gene grow as well as unsprayed control plants. For example, the herbicide glyphosate acts by inhibiting the enzyme 5-enolpyruvyl-3-phosphoshikimate synthase (EPSPS). Glyphosate tolerant plants have been produced by inserting EPSPS into the plant genome (U.S. Pat. No. 5,312,910).

Genetic engineering has also been used to protect plants from bacterial, fungal, and virus infection (D'Maris et. al., *Trends in Microbiol.* 6:54–61 (1998)). It has been shown that transgenic plants that express the coat protein of a virus become resistant to infection by that virus. Although the mechanism of resistance is unknown, the presence of viral coat protein in plant cells can interfere with the uncoating of viral particles containing that coat protein, thereby interrupting the virus replication cycle. Viral replicase and movement protein genes have also been used to confer resistance to viral pathogens. For example, mutated forms of viral genes may be added to the plant genome and expressed in plants for protection against viruses. U.S. Pat. No. 5,773,701 issued to Braun et al., describes the insertion of a potato virus X (PVX) replicase gene into a plant to confer resistance against PVX infection when the PVX replicase gene is sufficiently expressed. PCT publication WO 98/59046 describes the incorporation of β-glucanase gene in transgenic plants for increased resistance to fungal infection.

Proteins conferring insect resistance have also been genetically introduced into plants. Bt-toxins from *Bacillus thuringiensis* are toxic to moth, fly larvae, beetle, and mosquitoes. A Bt-toxin gene may be cloned into a plasmid vector under control of a chloroplast rRNA promoter and transferred into plant chloroplasts by particle bombardment. Plants that sufficiently express this protein are toxic to insect larvae.

The approach of using transgenic plants in acquiring herbicide, insect and disease resistance has many drawbacks. Because foreign genes are permanently inserted into the genome, development of transgenic plants can be costly and their durability could become a concern. In many cases, the targets of herbicides or pathogens are unknown and indirect. Therefore, finding suitable herbicide-specific or pathogen-specific targets is difficult.

The present invention features a method of using transient plant viral expression vectors to express enzymes or proteins to confer resistance to herbicides, pests, and diseases in plant hosts. Viruses are a unique class of infectious agents whose distinctive features are their simple organization and their mechanism of replication. Their hosts include a wide variety of plants. A complete viral particle, or virion, may be regarded mainly as a block of genetic material (either DNA or RNA) capable of autonomous replication, surrounded by a protein coat and sometimes by an additional membranous envelope. The coat protects the virus from the environment and serves as a vehicle for transmission from one host cell to another.

Virus-based expression systems, in which the foreign mRNA is greatly amplified by virus replication, can produce very high levels of proteins in leaves and other tissues. Viral vector produced protein can also be directed to specific subcellular locations, such as endomembrane, cytosol, or organelles, or it can be attached to macromolecules, such as virions. In addition, virus vectors are ideal for shuttling libraries of sequence variants throughout plant hosts for selection of resistance to herbicides, pests, and diseases.

SUMMARY OF THE INVENTION

In one aspect of this invention, recombinant viral nucleic acids are used to express foreign proteins or enzymes that confer resistance to herbicides, pests, and diseases. These foreign proteins or enzymes may be the direct or indirect targets of herbicides or pathogens. In particular, viral expression vectors may contain one or more non-native subgenomic promoters. Herbicides may include any compounds that affect the plant growth. Pathogens may include bacteria, fungi, viruses, insects, nematodes or arachnids, among others, which affect the plant growth.

In another aspect of the invention, a library containing nucleic acid sequence variants may be generated by in vivo or in vitro methods. A population of nucleic acid sequence variants may be represented by a genomic library, a cDNA library, or a pool of mRNA derived from bacteria, fungi, viruses, plants, or animals. In vitro mutagenesis or recombination methods may also be used to construct a library containing nucleic acid sequence variants. These methods may include chemical treatment, oligonucleotide mediated mutagenesis, error-prone PCR, combinatorial cassette mutagenesis, DNA shuffling, random-priming recombination, restriction enzyme fragment induced template switching, staggered extension process, among others. A library containing sequence variants may be expressed in plant hosts to screen sequences that confer resistance to herbicides, pests or diseases. The screening of sequence libraries is typically followed by rescue of the viruses from populations conferring desired resistance. If necessary, re-screening of sub-libraries may be performed. In preferred embodiments, sequences of the viral nucleic acids conferring desired resistance may be determined and compared with the control sequences. The expression of sequence libraries to select recombinant viral nucleic acids that confer resistance in plant hosts is particularly suited when the targets of herbicides or pathogens are unknown or less defined. This aspect of the invention is also applicable when the level of resistance in plant hosts is in need of modulation or optimization.

In another aspect of the invention, antisense technology may be used as a method to determine the targets of herbicides or pathogens in plant hosts. In essence, antisense RNA or DNA molecules bind endogenous mRNA, thereby turning off certain endogenous genes. A library of sequence variants may be applied to the plants to turn off endogenous proteins or enzymes in plant hosts like herbicides or pathogens. Targets of herbicides or pathogens may be determined by isolating and sequencing viral nucleic acids that affect the plant growth. Once the target enzymes or proteins are identified, they may be expressed in plant hosts using viral expression vectors to screen for desired resistance.

BRIEF DESCRIPTION OF THE FIGURES

FIG. 1 depicts the vector TTOSA1CTP CrtI 491.

FIG. 2 depicts the *Erwinia herbicola* phytoene desaturase gene (plasmid pAU211).

FIG. 3 depicts the plasmid KS+/CrtI* 491.

FIG. 4 depicts the plasmid pBS736.

FIG. 5 depicts the plasmid pBS 735.

FIG. 6 depicts the plasmid pBS 740.

FIG. 7 depicts the plasmid pBS 712.

DETAILED DESCRIPTION OF THE INVENTION

I. Genetic Backbone and Components of Viral Nucleic Acids

The construction of viral expression vectors may use a variety of methods known in the art. In preferred embodiments of the instant invention, the viral vectors are derived from RNA plant viruses. A variety of plant virus families may be used, such as Bromoviridae, Bunyaviridae, Comoviridae, Geminiviridae, Potyviridae, and Tombusviridae, among others. Within the plant virus families, various genera of viruses may be suitable for the instant invention, such as alfamovirus, ilarvirus, bromovirus, cucumovirus, tospovirus, carlavirus, caulimovirus, closterovirus, comovirus, nepovirus, dianthovirus, furovirus, hordeivirus, luteovirus, necrovirus, potexvirus, potyvirus, rymovirus, bymovirus, oryzavirus, sobemovirus, tobamovirus, tobravirus, carmovirus, tombusvirus, tymovirus, umbravirusa, and among others.

Within the genera of plant viruses, many species are particular preferred. They include alfalfa mosaic virus, tobacco streak virus, brome mosaic virus, broad bean mottle virus, cowpea chlorotic mottle virus, cucumber mosaic virus, tomato spotted wilt virus, carnation latent virus, caulflower mosaic virus, beet yellows virus, cowpea mosaic virus, tobacco ringspot virus, carnation ringspot virus, soil-borne wheat mosaic virus, tomato golden mosaic virus, cassava latent virus, barley stripe mosaic virus, barley yellow dwarf virus, tobacco necrosis virus, tobacco etch virus, potato virus X, potato virus Y, rice necrosis virus, ryegrass mosaic virus, barley yellow mosaic virus, rice ragged stunt virus, Southern bean mosaic virus, tobacco mosaic virus, ribgrass mosaic virus, cucumber green mottle mosaic virus watermelon strain, oat mosaic virus, tobacco rattle virus, carnation mottle virus, tomato bushy stunt virus, turnip yellow mosaic virus, carrot mottle virus, among others. In addition, RNA satellite viruses, such as tobacco necrosis satellite may also be employed.

A given plant virus may contain either DNA or RNA, which may be either single- or double-stranded. One example of plant viruses containing double-stranded DNA includes, but not limited to, caulimoviruses such as cauliflower mosaic virus (CaMV). Representative plant viruses which contain single-stranded DNA are cassava latent virus, bean golden mosaic virus (BGMV), and chloris striate mosaic virus. Rice dwarf virus and wound tumor virus are examples of double-stranded RNA plant viruses. Single-stranded RNA plant viruses include tobacco mosaic virus (TMV), turnip yellow mosaic virus (TYMV), rice necrosis virus (RNV) and brome mosaic virus (BMV). The single-stranded RNA viruses can be further divided into plus sense (or positive-stranded), minus sense (or negative-stranded), or ambisense viruses. The genomic RNA of a plus sense RNA virus is messenger sense, which makes the naked RNA infectious. Many plant viruses belong to the family of plus sense RNA viruses. They include, for example, TMV, BMV, and others. RNA plant viruses typically encode several common proteins, such as replicase/polymerase proteins essential for viral replication and mRNA synthesis, coat proteins providing protective shells for the extracellular passage, and other proteins required for the cell-to-cell movement, systemic infection and self-assembly of viruses. For general information concerning plant viruses, see Matthews, *Plant Virology*, $3^{rd}$ Ed., Academic Press, San Diego (1991).

Selected groups of suitable plant viruses are characterized below. However, the invention should not be construed as limited to using these particular viruses, but rather the method of the present invention is contemplated to include all plant viruses at a minimum.

Tobamovirus Group

Tobacco Mosaic virus (TMV) is a member of the Tobamoviruses. The TMV virion is a tubular filament, and comprises coat protein sub-units arranged in a single right-handed helix with the single-stranded RNA intercalated between the turns of the helix. TMV infects tobacco as well as other plants. TMV is transmitted mechanically and may remain infective for a year or more in soil or dried leaf tissue.

The TMV virions may be inactivated by subjection to an environment with a pH of less than 3 or greater than 8, or by formaldehyde or iodine. Preparations of TMV may be obtained from plant tissues by $(NH_4)_2SO_4$ precipitation, followed by differential centrifugation.

Tobacco mosaic virus (TMV) is a positive-stranded ssRNA virus whose genome is 6395 nucleotides long and is capped at the 5'-end but not polyadenylated. The genomic RNA can serve as mRNA for protein of a molecular weight of about 130,000 (130K) and another produced by read-through of molecular weight about 180,000 (180K). However, it cannot function as a messenger for the synthesis of coat protein. Other genes are expressed during infection by the formation of monocistronic, 3'-coterminal subgenomic mRNAs, including one (LMC) encoding the 17.5K coat protein and another ($I_2$) encoding a 30K protein. The 30K protein has been detected in infected protoplasts as described in Miller, J., *Virology* 132:71 (1984), and it is involved in the cell-to-cell transport of the virus in an infected plant as described by Deom et al., *Science* 237:389 (1987). The functions of the two large proteins are unknown, however, they are thought to function in RNA replication and transcription.

Several double-stranded RNA molecules, including double-stranded RNAs corresponding to the genomic, $I_2$ and LMC RNAs, have been detected in plant tissues infected with TMV. These RNA molecules are presumably intermediates in genome replication and/or mRNA synthesis processes which appear to occur by different mechanisms.

TMV assembly apparently occurs in plant cell cytoplasm, although it has been suggested that some TMV assembly may occur in chloroplasts since transcripts of ctDNA have been detected in purified TMV virions. Initiation of TMV assembly occurs by interaction between ring-shaped aggregates ("discs") of coat protein (each disc consisting of two layers of 17 subunits) and a unique internal nucleation site in the RNA; a hairpin region about 900 nucleotides from the 3'-end in the common strain of TMV. Any RNA, including subgenomic RNAs containing this site, may be packaged into virions. The discs apparently assume a helical form on interaction with the RNA, and assembly (elongation) then proceeds in both directions (but much more rapidly in the 3'- to 5'-direction from the nucleation site).

Another member of the Tobamoviruses, the Cucumber Green Mottle Mosaic virus watermelon strain (CGMMV-W) is related to the cucumber virus. Nozu et al., *Virology* 45:577 (1971). The coat protein of CGMMV-W interacts with RNA of both TMV and CGMMV to assemble viral particles in vitro. Kurisu et al., *Virology* 70:214 (1976).

Several strains of the tobamovirus group are divided into two subgroups, on the basis of the location of the origin of assembly. Subgroup I, which includes the vulgare, OM, and tomato strain, has an origin of assembly about 800–1000 nucleotides from the 3'-end of the RNA genome, and outside the coat protein cistron. Lebeurier et al., *Proc. Natl. Acad. Sci. USA* 74:149 (1977); and Fukuda et al., *Virology* 101:493 (1980). Subgroup II, which includes CGMMV-W and cowpea strain (Cc) has an origin of assembly about 300–500 nucleotides from the 3'-end of the RNA genome and within the coat protein cistron. The coat protein cistron of CGMMV-W is located at nucleotides 176–661 from the 3'-end. The 3' noncoding region is 175 nucleotides long. The origin of assembly is positioned within the coat protein cistron. Meshi et al., *Virology* 127:54 (1983).

Brome Mosaic Virus Group

Brome Mosaic virus (BMV) is a member of a group of tripartite, single-stranded, RNA-containing plant viruses commonly referred to as the bromoviruses. Each member of the bromoviruses infects a narrow range of plants. Mechanical transmission of bromoviruses occurs readily, and some members are transmitted by beetles. In addition to BMV, other bromoviruses include broad bean mottle virus and cowpea chlorotic mottle virus.

Typically, a bromovirus virion is icosahedral, with a diameter of about 26 μm, containing a single species of coat protein. The bromovirus genome has three molecules of linear, positive-sense, single-stranded RNA, and the coat protein mRNA is also encapsidated. The RNAs each have a capped 5'-end, and a tRNA-like structure (which accepts tyrosine) at the 3'-end. Virus assembly occurs in the cytoplasm. The complete nucleotide sequence of BMV has been identified and characterized as described by Ahlquist et al., *J. Mol. Biol.* 153:23 (1981).

Rice Necrosis Virus

Rice Necrosis virus is a member of the Potato Virus Y Group or Potyviruses. The Rice Necrosis virion is a flexuous filament comprising one type of coat protein (molecular weight about 32,000 to about 36,000) and one molecule of linear positive-sense single-stranded RNA. The Rice Necrosis virus is transmitted by *Polymyxa oraminis* (a eukaryotic intracellular parasite found in plants, algae and fungi).

Geminiviruses

Geminiviruses are a group of small, single-stranded DNA-containing plant viruses with virions of unique morphology. Each virion consists of a pair of isometric particles (incomplete icosahedral), composed of a single type of protein (with a molecular weight of about $2.7–3.4\times10^4$). Each geminivirus virion contains one molecule of circular, positive-sense, single-stranded DNA. In some geminiviruses (i.e., Cassava latent virus and bean golden mosaic virus) the genome appears to be bipartite, containing two single-stranded DNA molecules.

Potyviruses

Potyviruses are a group of plant viruses which produce polyprotein. A particularly preferred potyvirus is tobacco etch virus (TEV). TEV is a well characterized potyvirus and contains a positive-strand RNA genome of 9.5 kilobases encoding for a single, large polyprotein that is processed by three virus-specific proteinases. The nuclear inclusion protein "a" proteinase is involved in the maturation of several replication-associated proteins and capsid protein. The helper component-proteinase (HC-Pro) and 35-kDa proteinase both catalyze cleavage only at their respective C-termini. The proteolytic domain in each of these proteins is located near the C-terminus. The 35-kDa proteinase and HC-Pro derive from the N-terminal region of the TEV polyprotein.

The selection of the genetic backbone for the viral vectors of the instant invention may depend on the plant host used. The plant host may be a monocotyledonous or dicotyledonous plant, plant tissue, or plant cell. Typically, plants of commercial interest, such as food crops, seed crops, oil crops, ornamental crops and forestry crops are preferred. For example, wheat, rice, corn, potato, barley, tobacco, soybean canola, maize, oilseed rape, lilies, grasses, orchids, irises, onions, palms, tomato, the legumes, or *Arabidopsis*, can be used as a plant host. Host plants may also include those readily infected by an infectious virus, such as *Nicotiana*, preferably, *Nicotiana benthamiana*, or *Nicotiana clevelandii*.

One feature of the present invention is the use of plant viral nucleic acids which comprise one or more non-native nucleic acid sequences capable of being transcribed in a host plant. These nucleic acid sequences may be native nucleic acid sequences that occur in a host plant. Preferably, these nucleic acid sequences are non-native nucleic acid sequences that do not normally occur in a host plant. For example, the plant viral vectors may contain sequences from more than one virus, including viruses from more than one taxonomic group. The plant viral nucleic acids may also contain sequences from non-viral sources, such as foreign genes, regulatory sequences, fragments thereof from bacteria, fungi, plants, animals or other sources. These foreign sequences may encode commercially useful proteins, polypeptides, or fusion products thereof, such as enzymes, antibodies, hormones, pharmaceuticals, vaccines, pigments, antimicrobial polypeptides and the like. Or they may be sequences that regulate the transcription or translation of viral nucleic acids, package viral nucleic acid, and facilitate systemic infection in the host, among others. They may also encode direct or indirect target proteins or enzymes of herbicides or pathogens.

In some embodiments of the instant invention, the plant viral vectors may comprise one or more additional native or non-native subgenomic promoters which are capable of transcribing or expressing adjacent nucleic acid sequences in the plant host. These non-native subgenomic promoters are inserted into the plant viral nucleic acids without destroying the biological function of the plant viral nucleic acids using known methods in the art. For example, the CaMV promoter can be used when plant cells are to be transfected. The subgenomic promoters are capable of functioning in the specific host plant. For example, if the host is tobacco, TMV, tomato mosaic virus, or other viruses containing subgenomic promoter may be utilized. The inserted subgenomic promoters should be compatible with the TMV nucleic acid and capable of directing transcription or expression of adjacent nucleic acid sequences in tobacco. It is specifically contemplated that two or more heterologous non-native subgenomic promoters may be used. The non-native nucleic acid sequences may be transcribed or expressed in the host plant under the control of the subgenomic promoter to produce the products of the nucleic acids of interest.

Since the RNA genome is typically the infective agent, the cDNA is positioned adjacent a suitable promoter so that the RNA is produced in the production cell. The RNA is capped using conventional techniques, if the capped RNA is the infective agent. In addition, the capped RNA can be packaged in vitro with added coat protein from TMV to make assembled virions. These assembled virions can then be used to inoculate plants or plant tissues. Alternatively, an uncapped RNA may also be employed in the embodiments of the present invention. Contrary to the practiced art in scientific literature and in issued patent (Ahlquist et al., U.S. Pat. No. 5,466,788), uncapped transcripts for virus expression vectors are infective on both plants and in plant cells. Capping is not a prerequisite for establishing an infection of a virus expression vector in plants, although capping increases the efficiency of infection. In addition, nucleotides may be added between the transcription start site of the promoter and the start of the cDNA of a viral nucleic acid to construct an infectious viral vector. One or more nucleotides may be added. In some embodiments of the present invention, the inserted nucleotide sequence may contain a G at the 5'-end. Alternatively, the inserted nucleotide sequence may be GNN, GTN, or their multiples, $(GNN)_x$ or $(GTN)_x$.

In some embodiments of the instant invention, more than one nucleic acid is prepared for a multipartite viral vector construct. In this case, each nucleic acid may require its own origin of assembly. Each nucleic acid could be prepared to contain a subgenomic promoter and a non-native nucleic acid. Alternatively, the insertion of a non-native nucleic acid into the nucleic acid of a monopartite virus may result in the creation of two nucleic acids (i.e., the nucleic acid necessary for the creation of a bipartite viral vector). This would be advantageous when it is desirable to keep the replication and transcription or expression of the nucleic acid of interest separate from the replication and translation of some of the coding sequences of the native nucleic acid.

The recombinant plant viral nucleic acid may be prepared by cloning a viral nucleic acid. If the viral nucleic acid is DNA, it can be cloned directly into a suitable vector using conventional techniques. One technique is to attach an origin of replication to the viral DNA which is compatible with the cell to be transfected. In this manner, DNA copies of the chimeric nucleotide sequence are produced in the transfected cell. If the viral nucleic acid is RNA, a DNA copy of the viral nucleic acid is first prepared by well-known procedures. For example, the viral RNA is transcribed into DNA using reverse transcriptase to produce subgenomic DNA pieces, and a double-stranded DNA may be produced using DNA polymerases. The cDNA is then cloned into appropriate vectors and cloned into a cell to be transfected. In some instances, cDNA is first attached to a promoter which is compatible with the production cell. The recombinant plant viral nucleic acid can then be cloned into any suitable vector which is compatible with the production cell. Alternatively, the recombinant plant viral nucleic acid is inserted in a vector adjacent a promoter which is compatible with the production cell. In some embodiments, the cDNA ligated vector may be directly transcribed into infectious RNA in vitro and inoculated onto the plant host. The cDNA pieces are mapped and combined in proper sequence to produce a full-length DNA copy of the viral RNA genome, if necessary.

In some embodiments of the instant invention, increased the representation of gene sequences in virus expression libraries may also be achieved by bypassing the genetic bottleneck of propagation in bacterial cells. For example, in some embodiments of the instant invention, cell-free methods may be used to assemble sequence libraries or individual arrayed sequences into virus expression vectors and reconstruct an infectious virus, such that the final ligation product can be transcribed and the resulting RNA can be used for plant, plant tissue or plant cell inoculation/infection. A more detailed discussion is presented in a co-pending and co-owned U.S. patent application Ser. No. 09/359,303 (Padgett et al., incorporated herein by reference), now abandoned.

Those skilled in the art will understand that these embodiments are representative only of many constructs suitable for the instant invention. All such constructs are contemplated and intended to be within the scope of the present invention. The invention is not intended to be limited to any particular viral constructs but specifically contemplates using all operable constructs. A person skilled in the art will be able to construct the plant viral nucleic acids based on molecular biology techniques well known in the art. Suitable techniques have been described in Sambrook et al. (2nd ed.), Cold Spring Harbor Laboratory Cold Spring Harbor (1989); *Methods in Enzymol.* (Vols. 68, 100, 101, 118, and 152–155) (1979, 1983, 1986 and 1987); and *DNA Cloning*, D. M. Clover, Ed., IRL Press, Oxford (1985); Walkey, *Applied Plant Virology*, Chapman & Hall (1991); Matthews, *Plant Virology*, $3^{rd}$ Ed., Academic Press, San Diego (1991); Turpen et al., *J of Virological Methods*, 42:227–240 (1993); U.S. Pat. Nos. 4,885,248, 5,173,410, 5,316,931, 5,466,788, 5,491,076, 5,500,360, 5,589,367, 5,602,242, 5,627,060, 5,811,653, 5,866,785, 5,889,190, and 5,589,367, U.S. patent application Ser. No. 08/324,003, filed Oct. 14, 1004, now U.S. Pat. No. 5,977,438. Nucleic acid manipulations and enzyme treatments are carried out in accordance with manufacturers' recommended procedures in making such constructs.

II. Generating Libraries of Nucleic Acid Sequence Variants

One skilled in the art will appreciate that there are many ways to generate sequence variants. A population of nucleic acid sequence variants may be a genomic library, or cDNA library, or a pool of RNA derived from bacteria, fungi, viruses plants, or animals. Full-length cDNAs or genomic DNA can be obtained from public or private repositories, for example from Clontech (Palo Alto, Calif.). Alternatively, cDNA library can be prepared from a field sample by methods known to a person of ordinary skill, for example, isolating mRNAs and transcribing mRNAs into cDNAs by reverse transcriptase (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)). Genomic DNAs represented in BAC (bacterial artificial chromosome), YAC (yeast artificial chromosome), or TAC (transformation-competent artificial chromosome, Lin et al., *Proc. Natl. Acad. Sci. USA*, 96:6535–6540 (1999)) libraries may also be obtained from public or private repositories. The BAC/YAC/TAC DNAs, DNAs or cDNAs can be mechanically size-fractionated or digested by an enzyme to smaller fragments. The fragments are ligated to adapters with cohesive ends, and shotgun-cloned into recombinant viral nucleic acid vectors. Alternatively, the fragments can be blunt-end ligated into recombinant viral nucleic acid vectors. Recombinant plant viral nucleic acids containing a nucleic acid sequence derived from the cDNA library or genomic DNA library is then constructed using conventional techniques.

One or more template sequences may be used to generate libraries of nucleic acid sequence variants via in vitro mutagenesis, recombination or a combination thereof. These in vitro methods include chemical treatment, oligonucleotide mediated mutagenesis, PCR mutagenesis, DNA shuffling, random-priming recombination, restriction enzyme fragment induced template switching, staggered extension process, among others. The sequence populations may be random or selectively varied. In some embodiments of the invention, the template sequences may be derived from elements of plant viruses, such as the coat protein, movement protein, or replicase, among others. It is known that mutated forms of viral structural or non-structural proteins may be expressed in plants for resistance against viruses. In some embodiments of the invention, genes, regulatory sequences, or fragments thereof from sources such as bacteria, fungi, plants, animals, plant and animal viruses may serve as template sequences for generating sequence variants. For example, sequences encoding target proteins or enzymes of herbicides or pathogens may be used as template sequences. Sequences regulating the transcription and translation of the targets of herbicides or pathogens may also be used as template sequences.

A detailed discussion of methods for generating libraries of nucleic acid sequence variants is presented in two co-pending and co-owned U.S. patent application Ser. Nos. 09/359,297 and 09/359,304 (both incorporated herein by reference).

III. Expressing Viral Expression Vectors in Plant Hosts

Recombinant viral nucleic acids encoding resistance-specific proteins or enzymes can be transfected as populations or individual clones into host: 1) protoplasts; 2) whole plants; or 3) plant tissues, such as leaves of plants (Dijkstra et al., *Practical Plant Virology: Protocols and Exercises*, Springer Verlag (1998); *Plant Virology Protocol: From Virus Isolation to Transgenic Resistance* in *Methods in Molecular Biology*, Vol. 81, Foster and Taylor, Ed., Humana Press (1998)). The plant host may be a monocotyledonous or dicotyledonous plant, plant tissue, or plant cell. Typically, plants of commercial interest, such as food crops, seed crops, oil crops, ornamental crops and forestry crops are preferred. For example, wheat, rice, corn, potato, barley, tobacco, soybean canola, maize, oilseed rape, lilies, grasses, orchids, irises, onions, palms, tomato, the legumes, or *Arabidopsis*, can be used as a plant host. Host plants may also include those readily infected by an infectious virus, such as *Nicotiana*, preferably, *Nicotiana benthamiana*, or *Nicotiana clevelandii.*

In some embodiments of the instant invention, the delivery of the plant virus expression vectors into the plant may be affected by the inoculation of in vitro transcribed RNA, inoculation of virions, or internal inoculation of plant cells from nuclear cDNA, or the systemic infection resulting from any of these procedures. In all cases, the co-infection may lead to a rapid and pervasive systemic expression of the desired nucleic acid sequences in plant cells. The systemic infection of the plant by the foreign sequences may be followed by the growth of the infected host to produce the desired product, and the isolation and purification of the desired product, if necessary. The growth of the infected host is in accordance with conventional techniques, as is the isolation and the purification of the resultant products.

The host can be infected with a recombinant viral nucleic acid or a recombinant plant virus by conventional techniques. Suitable techniques include, but are not limited to, leaf abrasion, abrasion in solution, high velocity water spray, and other injury of a host as well as imbibing host seeds with water containing the recombinant viral RNA or recombinant plant virus. More specifically, suitable techniques include:

(a) Hand Inoculations. Hand inoculations are performed using a neutral pH, low molarity phosphate buffer, with the addition of celite or carborundum (usually about 1%). One to four drops of the preparation is put onto the upper surface of a leaf and gently rubbed.

(b) Mechanized Inoculations of Plant Beds. Plant bed inoculations are performed by spraying (gas-propelled) the vector solution into a tractor-driven mower while cutting the leaves. Alternatively, the plant bed is mowed and the vector solution sprayed immediately onto the cut leaves.

(c) High Pressure Spray of Single Leaves. Single plant inoculations can also be performed by spraying the leaves with a narrow, directed spray (50 psi, 6–12 inches from the leaf) containing approximately 1% carborundum in the buffered vector solution.

(d) Vacuum Infiltration. Inoculations may be accomplished by subjecting a host organism to a substantially vacuum pressure environment in order to facilitate infection.

(e) High Speed Robotics Inoculation. Especially applicable when the organism is a plant, individual organisms may be grown in mass array such as in microtiter plates. Machinery such as robotics may then be used to transfer the nucleic acid of interest.

(f) Ballistics (High Pressure Gun) Inoculation. Single plant inoculations can also be performed by particle bombardment. A ballistics particle delivery system (BioRad Laboratories, Hercules, (A) can be used to transfect plants such as *N. benthamiana* as described previously (Nagar et al., *Plant Cell*, 7:705–719 (1995)).

An alternative method for introducing viral nucleic acids into a plant host is a technique known as agroinfection or *Agrobacterium*-mediated transformation (also known as Agro-infection) as described by Grimsley et al, *Nature* 325:177 (1987). This technique makes use of a common feature of *Agrobacterium* which colonizes plants by transferring a portion of their DNA (the T-DNA) into a host cell, where it becomes integrated into nuclear DNA. The T-DNA is defined by border sequences which are 25 base pairs long, and any DNA between these border sequences is transferred to the plant cells as well. The insertion of a recombinant plant viral nucleic acid between the T-DNA border sequences results in transfer of the recombinant plant viral nucleic acid to the plant cells, where the recombinant plant viral nucleic acid is replicated, and then spreads systemically through the plant. Agro-infection has been accomplished with potato spindle tuber viroid (PSTV) (Gardner et al., *Plant Mol. Biol.* 6:221 (1986); CaV (Grimsley et al., *Proc. Natl. Acad. Sci. USA* 83:3282 (1986)); MSV (Grimsley et al., *Nature* 325:177 (1987)), and Lazarowitz, S., *Nucl. Acids Res.* 16:229 (1988)) digitaria streak virus (Donson et al., *Virology* 162:248 ( 1988)), wheat dwarf virus (Hayes et al., *J. Gen. Virol.* 69:891 (1988)) and tomato golden mosaic virus (TGMV) (Elmer et al., *Plant Mol. Biol.* 10:225 (1988) and Gardiner et al., *EMBO J.* 7:899 ( 1988)). Therefore, agro-infection of a susceptible plant could be accomplished with a virion containing a recombinant plant viral nucleic acid based on the nucleotide sequence of any of the above viruses. Particle bombardment or electrosporation or any other methods known in the art may also be used.

In some embodiments of the instant invention, infection may also be attained by placing a selected nucleic acid sequence into an organism such as *E. coli*, or yeast, either integrated into the genome of such organism or not, and then applying the organism to the surface of the host organism. Such a mechanism may thereby produce secondary transfer of the selected nucleic acid sequence into a host organism. This is a particularly practical embodiment when the host organism is a plant. Likewise, infection may be attained by first packaging a selected nucleic acid sequence in a pseudovirus. Such a method is described in WO 94/10329. Though the teachings of this reference may be specific for bacteria, those of skill in the art will readily appreciate that the same procedures could easily be adapted to other organisms.

IV. Conferring Resistance or Screening and Selecting for Resistance to Herbicides, Pests, or Diseases.

In one aspect of the invention, transient expression of recombinant viral nucleic acids encoding target proteins or enzymes of herbicides or pathogens may confer resistance to herbicides, pests, or diseases in plant hosts. Pathogens may include bacteria, fungi, viruses, insects, nematodes or arachnids, among others that affect the plant growth. Herbicides may include any compounds that affect the plant growth.

One skilled in the art will appreciate that there are many known genes that encode antimicrobial or pesticidal proteins/polypeptides and many genes have also been identified to induce antimicrobial or pesticidal activities (Bonas et al., *Curr. Opin. Microbiol.* 2:94–98 (1999); Ackerveken et al., *Trends Micorbiol.* 5:394–398 (1997); Baker et al., *Science* 276:726–733 (1997) and Durner et al., *Trends Plant Sci.*, 2:266–274 (1997)). For example, PR (pathogenenesis-related) proteins may exhibit antifungal activities (Kombrink et al. in *The Mycota* (Vol. 5A, Plant Relationships), Carrol and Tudzynski, Eds. pp. 107–128, Springer-Verlag (1997) and Stintzi et al., *Biochimie* 75:687–706 (1993)). PR proteins may include PR-1, PR-2 (1,3-β-glucanases), PR-3 (type I and II chitinases), PR-4, PR-5, PR-6 (proteinase inhibitors), PR-7 (proteinases), PR-8 (class III chitinases), PR-9 (peroxidases), PR-10, among others.

Phytoalexins are low molecular weigh compounds with antibacterial and antifungal activities in plant hosts (Kuc, *Annu. Rev. Phytopathol.* 33:275–297 (1995), Hain et al., *Nature* 361:153–156 (1993), and Dixon et al., in *Molecular Methods in Plant Pathology*, Singh and Singh, Eds., pp. 249–270, Lewis (1995)). Producing phytoalexins using viral expression vectors may require the expression of multiple genes.

Thionins are small, cysteine-rich polypeptides that exhibit antibacterial and antifingal activities in plant hosts (Bohlmann et al., *Crit. Rev. Plant Sci.*, 13:1–16 (1994) and Epple et al., *Plant Cell* 9:509–520 (1997). They may be expressed in the seed endosperm, stems, roots and etiolated or pathogen-stressed leaves. Defensins are another class of cysteine-rich proteins that efficiently inhibit the growth of a broad range of fungi (Broekaert et al., *Plant Physiol.* 108:1353–1358 (1995) and Shah et al., *Curr. Opin. Biotechnol.* 8:208–214 (1997)).

Insecticidal proteins may include δ-endotoxins from *B. thuringiensis* (BT)), or non-BT proteins, such as Vip3A, cholesterol oxidases, α-A1 amylase inhibitors, systemic-wound-response proteins, serine protease inhibitors I and II, trypsin inhibitors, among others ((Estruch et al., *Nat. Biotechnol.* 15:137–141 (1997); Shah et al., *Trends Biotechnol.* 13:362–368 (1995) enzymes such as chitinase, β-1,3-glucanase may also be used in plant resistance to insects as chitin is present in the exoskeleton of insects (Ryan, *Ann. Rev. Cell. Biol.* 3:295:317 (1987)).

Examples of herbicide compounds include EPSPS-inhibiting, acetolactate synthase (ALS)-inhibiting, protoporphyrinogen oxidase (PPO)-inhibiting, and Acetohydroxyacid synthase (AHAS)-inhibiting herbicides, among others. EPSPS is involved in the synthesis of aromatic amino acids. EPSPS inhibiting herbicide compounds may include various forms of N-phosphonomethylglycine among others. ALS is an enzyme common to the biosynthesis of branched amino acids (valine, leucine, and isoleucine). It affects many species of bacteria, fungi, yeasts, plants, and algae. ALS-inhibiting herbicide compounds include sulfonylureas, imidazolinone, triazolopyrimidine, pyrimidyloxybenzoate and phthalide, among others. PPO catalyzes the oxidation of protoporphyrinogen IX to protoporphyrin IX. This enzyme is commonly found in microorganisms and plants. PPO-inhibiting herbicide compounds, or the prophyric herbicides, are disclosed in WO 98/29554. AHAS catalyzes the first step in the synthesis of branched amino acids. It is common to the aspartate and branched amino acid pathways in microorganisms and plants (U.S. Pat. No. 5,718,079). AHAS-inhibiting herbicides may include imidazolinones, sulfonamides, among others.

Transient expression of direct or indirect target molecules of herbicides or pathogens in plant hosts using the viral expression vectors may confer resistance to herbicides, pests, or diseases. However, if the target molecules of herbicides or pathogens are unknown or uncharacterized, a plant host may be infected with a population of sequence variants to select for resistance to herbicides or pathogens. The screening of sequence libraries is typically followed by rescue of the viruses from populations conferring desired resistance. If necessary, re-screening of sub-libraries may be performed. In some embodiments, sequences of the viral nucleic acids conferring desired resistance may be determined and compared with the template or control sequences. The advantages of expressing a library of sequence variants in plant hosts is that the targets of herbicides or pathogens do not need to be identified, known, or characterized prior to infecting a host plant with a recombinant viral nucleic acid comprising the nucleic acid sequence variants.

To screen the desired resistance, biochemical or phenotypic changes in a plant host is determined. The biochemical or phenotypic changes in the infected host plant may be correlated to the biochemistry or phenotype of a host plant that is uninfected. Optionally, the biochemical or phenotypic changes in the infected host plant is further correlated to a host plant that is infected with a viral vector that contains a control nucleic acid of a known sequence. The phenotypic changes in a plant host may be determined by any known methods in the art. Typically, these methods include visual, morphological, macroscopic or microscopic analysis. For example, growth changes, such as stunting, color changes (e.g. leaf yellowing, mottling, bleaching, chlorosis) among others are easily visualized. Examples of morphological changes include, developmental defects, wilting, necrosis, among others. Biochemical changes can be determined by any analytical methods known in the art for detecting, quantitating, or isolating DNA, RNA, proteins, antibodies, carbohydrates, lipids, and small molecules. Selected methods may include Northern, Western blotting, MALDI-TOF, LC/MS, GC/MS, two-dimensional IEF/SDS-PAGE, ELISA, etc. In particular, suitable methods may be performed in a high-throughput, fully automated fashion using robotics. Examples of biochemical changes may include the accumulation of substrates or products from enzymatic reactions, changes in biochemical pathways, inhibition or augmentation of endogenous gene expression in the cytoplasm of cells, changes in the RNA or protein profile.

Those of skill in the art will readily understand that there are many methods to determine phenotypic or biochemical changes in a plant host and to select one or more viral nucleic acids that exhibit the desired resistance. In some embodiments, plant hosts capable of growing or maintaining viability in the presence of herbicides or pathogens may be selected and recombinant viral nucleic acids infecting such plant hosts may be sequenced and used for conferring resistance to herbicides, pests, or diseases. The selected sequences may also be used as the starting template sequences for re-screening.

In another aspect of the invention, antisense technology may be used as a method to determine the targets of herbicides or pathogens in plant hosts. In essence, antisense RNA or DNA molecules bind mRNA, thereby turning off certain endogenous genes. A library of sequence variants may be applied to the plants to turn off endogenous proteins or enzymes in plant hosts like herbicides or pathogens. Targets of herbicides or pathogens may be determined by isolating and sequencing viral nucleic acids that affect the plant growth. Once the target enzymes or proteins are identified, they may be expressed in plant hosts using viral expression vectors to screen for desired resistance in a sense orientation. Detail discussions of the screening in sense and antisense orientations are described in two co-pending and co-owned U.S. patent application Ser. Nos. 09/359,301, filed Jul. 21, 1999, now U.S. Pat. No. 6,246,185 and Ser. No. 09/359,305, filed Jul. 21, 1999, now abandoned (both incorporated herein by reference).

In order to provide a clear and consistent understanding of the specification and the claims, including the scope given herein to such terms, the following definitions are given:

Anti-Sense Inhibition: A type of gene regulation based on cytoplasmic, nuclear or organelle inhibition of gene expression due to the presence in a cell of an RNA molecule complementary to at least a portion of the mRNA being translated. It is specifically contemplated that RNA molecules may be from either an RNA virus or mRNA from the host cells genome or from a DNA virus.

Coat protein (capsid protein): an outer structural protein of a virus.

Dual Heterologous Subgenomic Promoter Expression System (DHSPES): a plus stranded RNA vector having a dual heterologous subgenomic promoter expression system to increase, decrease, or change the expression of proteins, peptides or RNAs, preferably those described in U.S. Pat. Nos. 5,316,931, 5,811,653, 5,589,367, and 5,866,785, the disclosure of which is incorporated herein by reference.

Expression: The term as used herein is meant to incorporate one or more of transcription, reverse transcription and translation.

Gene: a discrete nucleic acid sequence responsible for a discrete cellular product.

Host: a cell, tissue or organism capable of replicating a vector or viral nucleic acid and which is capable of being infected by a virus containing the viral vector or viral nucleic acid. This term is intended to include prokaryotic and eukaryotic cells, organs, tissues or organisms, or in vitro extracts thereof, where appropriate.

Infection: the ability of a virus to transfer its nucleic acid to a host or introduce viral nucleic acid into a host, wherein the viral nucleic acid is replicated, viral proteins are synthesized, and new viral particles assembled.

Movement protein: a noncapsid protein required for cell-to-cell movement of RNA replicons or viruses in plants.

Non-native (foreign): any sequence that does not normally occur in the virus or its host.

Open Reading Frame: a nucleotide sequence of suitable length in which there are no stop codons.

Plant Cell: the structural and physiological unit of plants, consisting of a protoplast and the cell wall.

Plant Tissue: any tissue of a plant in planta or in culture. This term is intended to include a whole plant, plant cell, plant organ, protoplast, cell culture, or any group of plant cells organized into a structural and functional unit. This term include, but not limited to, roots, shoots, leaves, pollen, embryos, seed and various forms of aggregations of plant cells including callus.

Promoter: the 5'-flanking, non-coding sequence adjacent to a coding sequence which is involved in the initiation of transcription of the coding sequence.

Protoplast: an isolated cell without cell walls, having the potency for regeneration into cell culture or a whole host.

Subgenomic mRNA promoter: a promoter that directs the synthesis of an mRNA smaller than the full-length genome in size.

Transient expression: Expression of a nucleic acid sequence in a host without insertion of the nucleic acid sequence into the host genome, such as by way of a viral vector.

Vector: a self-replicating nucleic acid molecule that contains non-native sequences and which transfers nucleic acids between cells.

Virion: a particle composed of viral nucleic acid, viral coat protein (or capsid protein).

Virus: an infectious agent composed of a nucleic acid encapsulated in a protein.

EXAMPLES OF THE PREFERRED EMBODIMENTS

The following examples further illustrate the present invention. These examples are intended merely to be illustrative of the present invention and are not to be construed as being limiting.

Example 1

Expression of Bacterial Phytoene Desaturase (CrtI) Gene in Transfected Plants Confers Resistance to Norflurazon Herbicide.

*Erwinia* phytoene desaturase (PDS), which is encoded by the gene CrtI (Armstrong et al., *Proc. Natl. Acad. Sci. USA* 87:9975–9979 (1990) and Armstrong et al., *J. Biol. Chem.*

Figure 1:
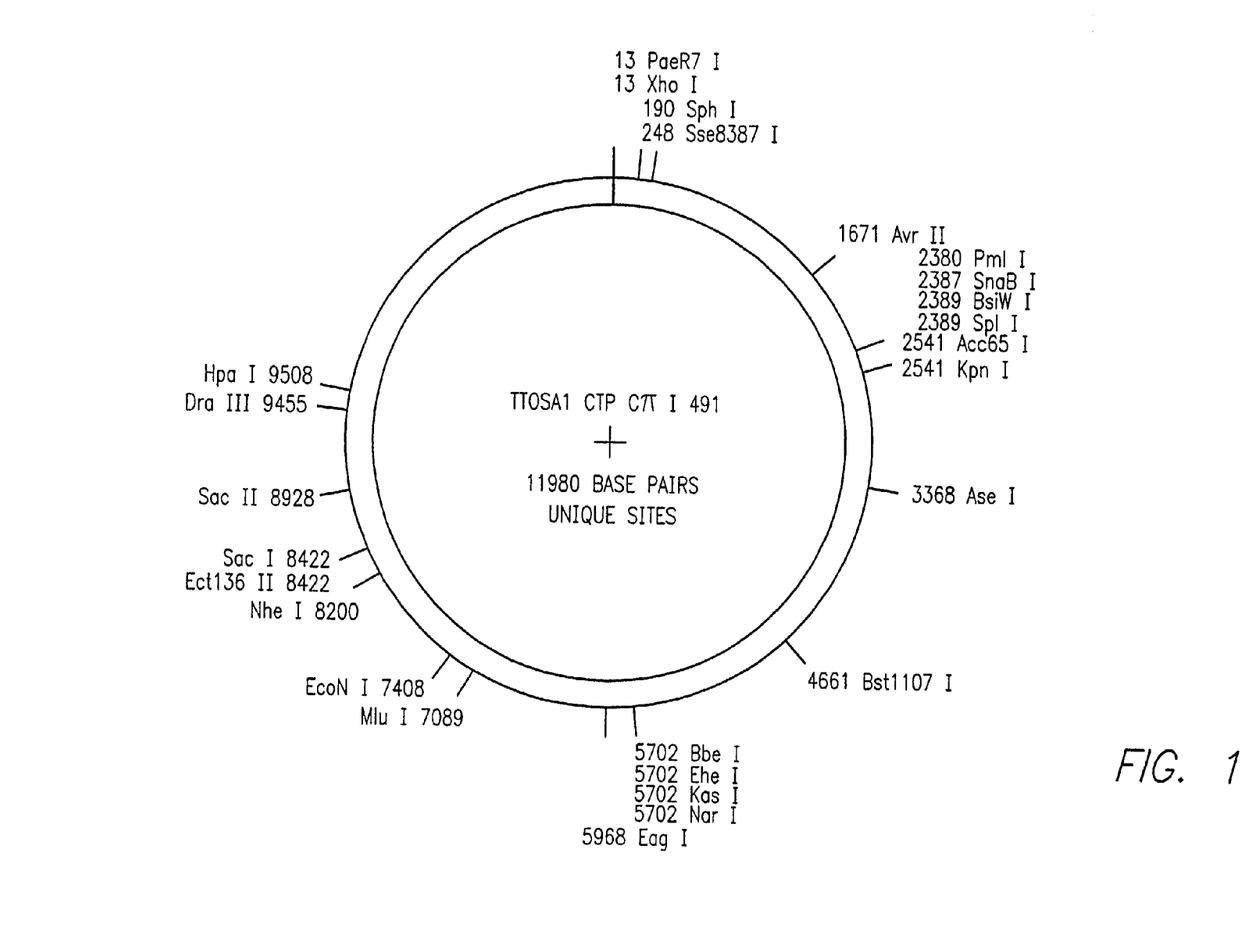

265:8329–8 (1990)), converts phytoene to lycopene through four desaturation steps. While plant PDS is sensitive to the bleaching herbicide norflurazon, *Erwinia* PDS is not inhibited by norflurazon (Misawa et al., *Plant J.* 6(4):481–489 (1994)). The open reading frame (ORF) for CrtI was placed under the control of the tobacco mosaic virus (TMV) coat protein subgenomic promoter in the vector TTOSA1. This construct also contained the gene encoding the chloroplast targeting peptide (CTP) for the small subunit of ribulose-1, 5-bisphosphate carboxylase (RUBISCO) and was called TTOSA1 CTP CrtI 491 #7 Infectious RNA was prepared by in vitro transcription using SP6 DNA-dependent RNA polymerase (Dawson et al., *Proc. Natl. Acad. Sci. USA* 83:1832–1836 (1986)) and was used to mechanically inoculate *N. benthamiana*. The hybrid virus spread throughout all the non-inoculated upper leaves, conferring resistance to norflurazon to the entire plant. TTOSA1 CTP CrtI 491 #7 (FIG. 1) inoculated plants remained green instead of bleaching white, and maintained higher levels of β-carotene compared to uninoculated control plants.

Plasmid Constructions.

Figure 2:
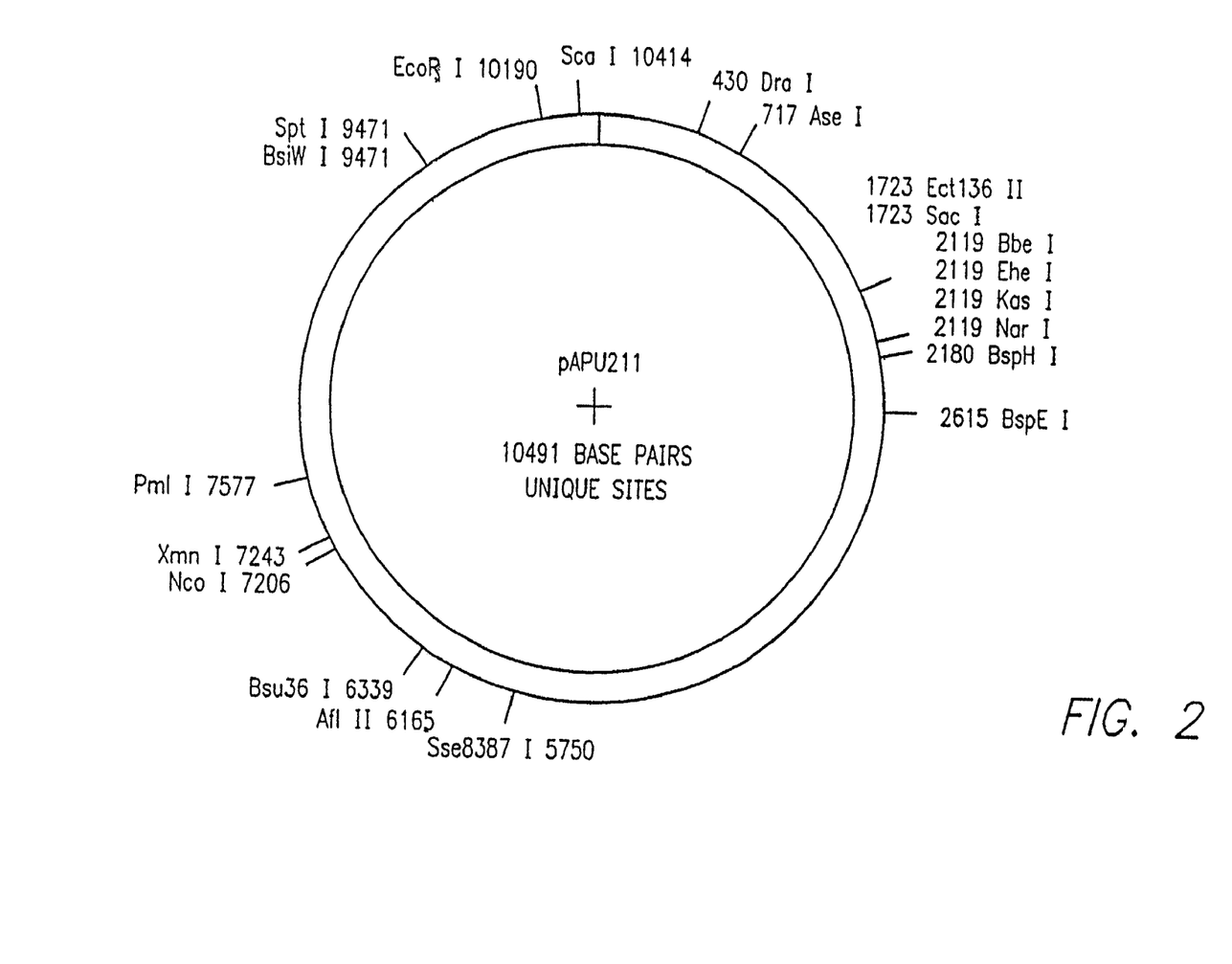
Figure 3:
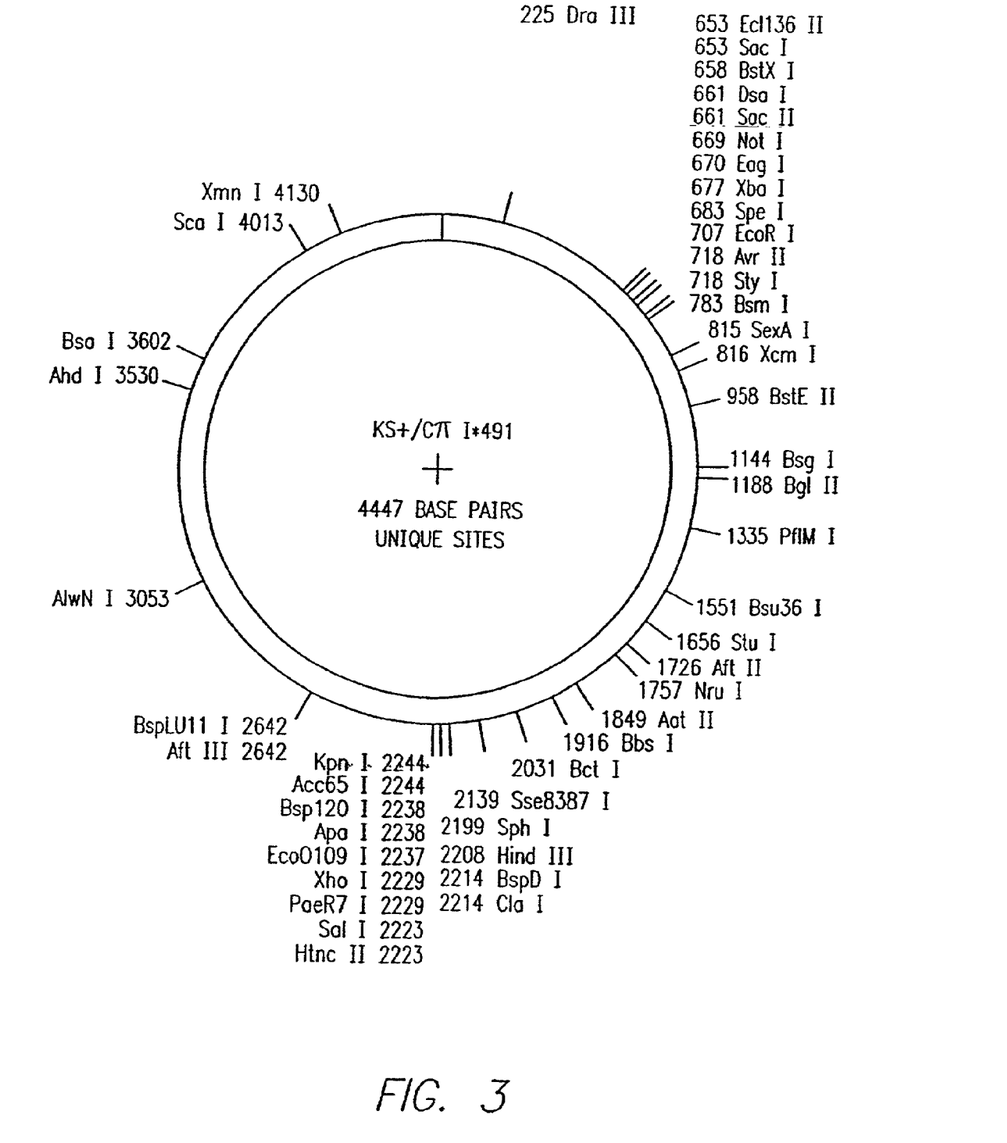

The chloroplast targeting, bacterial phytoene desaturase expression vector, TTOSA1 CTP CrtI 491 #7 was constructed as follows. First, a unique SphI site was inserted in the start codon for the *Erwinia herbicola* phytoene desaturase gene (plasmid pAU211, (FIG. 2) by polymerase chain reaction (PCR) mutagenesis using the oligonucleotides CrtI HSM1 5'-GA CAG AAG CTT TGC AGC ATG CAA AAA ACC GTT-3' (upstream) (SEQ ID NO: 1) and IQ419A 5'-CGC GGT CAT TGC AGA TCC TCA ATC ATC AGG C-3' (downstream) (SEQ ID NO: 2). The 1504 bp CrtI PCR fragment was subcloned into pBluescript® (Stratagene) by inserting it between the EcoRV and HindIII sites, creating plasmid KS+/CrtI* 491 (FIG. 3). A 1481 bp SphI, AvrIII CrtI fragment from plasmid KS+/CrtI* 491 was then subcloned into the tobamoviral vector TTOSA1, creating TTOSA1 CTP CrtI 491 #7.

Treatment of Transfected Plants with Norflurazon and Results.

Starting 7 days after viral inoculation, the plants were treated with 5 ml of a 10 mg/ml Solicam®DF (Sandoz Agro, Inc.) norflurazon herbicide solution [(4-chloro-5-(methylamino)-2-(alpha, alpha, alpha-trifluoro-m-tolyl)-3(2H)-pyridazinone)] every 4 days by applying to leaves and soil. Five days after initiating treatment, uninfected plants were almost entirely white, especially in the upper leaves and meristematic areas. Plants infected with TTOSA1 CTP CrtI 491 #7 were still green and were almost identical in appearance to the non-norflurazon treated infected controls.

Leaf Analysis.

The spread of the virally expressed CrtI gene throughout the plant was verified by Northern blotting. Viral RNA was purified from uninoculated upper leaves and was probed with the 1.5 kb CrtI gene. Positive results were obtained from plants inoculated with TTOSA1 CTP CrtI 491 #7.

Leaf tissue from a TTOSA1 CTP CrtI 491 #7 infected plant was examined for β-carotene levels. Treating an uninoculated control plant with norflurazon resulted in severely depressed β-Pcarotene levels (7.8% of the wild-type level). However, when a plant which had been previously inoculated with the viral construct TTOSA1 CTP CrtI 491 #7 was treated with norflurazon, the β-carotene level were partially restored (28.3% of the wild-type level). This is similar to the level of β-carotene in TTOSA1 CTP CrtI 491 #7 samples not treated with norflurazon (an average of 38.3% of wild-type), indicating that the herbicide norflurazon had little effect on β-carotene levels in previously transfected plants. The expression of the bacterial phytoene desaturase in systematically infected tissue conferred resistance to the herbicide norflurazon.

Example 2

Expression of 5-enolpyruvylshikimate-3-phosphate synthase (EPSPS) Genes in Plants Confers Resistance to N-(Phosphonomethyl)glycine isopropylamine salt (Roundup® Herbicide).

Figure 4:
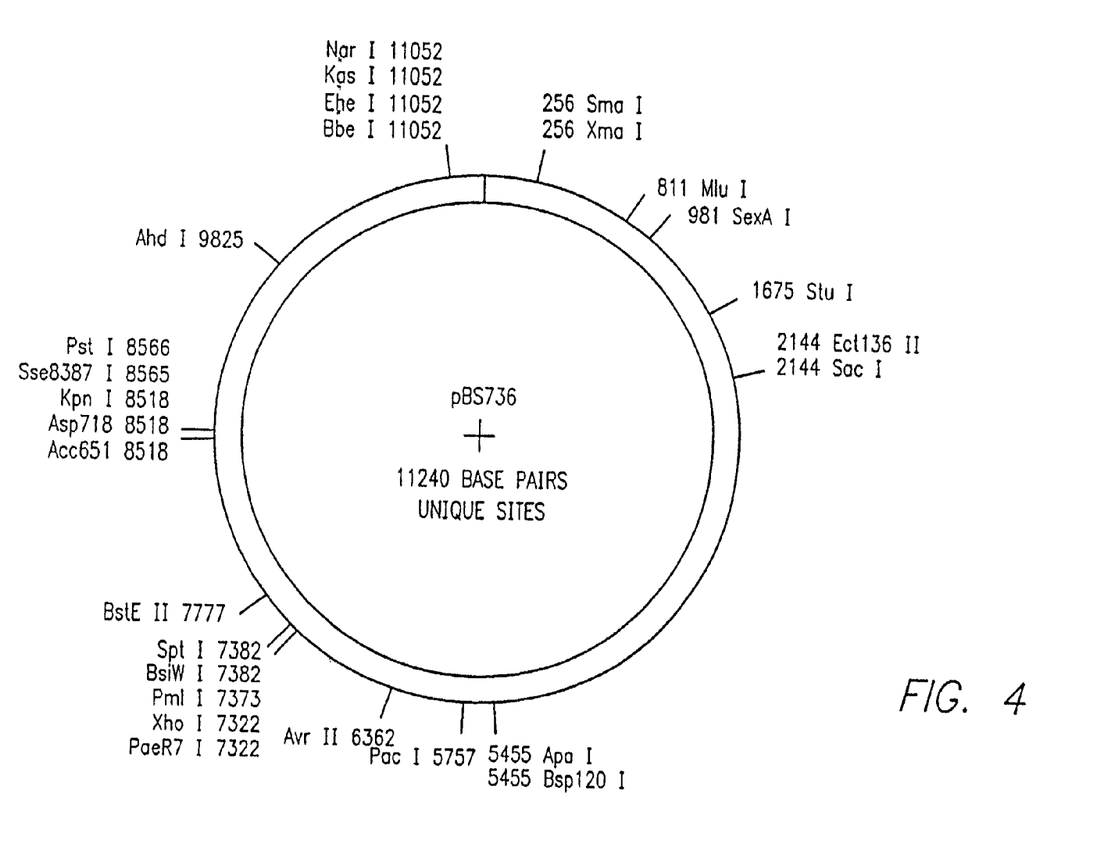

Systemic expression via a recombinant viral vector of 5-enolpyruvylshikimate-3-phosphate synthase (EPSPS) genes in plants confers resistance to N-(Phosphonomethyl) glycine, isopropylamine salt, which is the chemical name for the product known as Roundup® herbicide. See also della-Cioppa, et al., "Genetic Engineering of herbicide resistance in plants," *Frontiers of Chemistry: Biotechnology*, Chemical Abstract Service, ACS, Columbus, Ohio, pp. 665–70 (1989). The purpose of this experiment is to provide a method to systemically express EPSPS genes via a recombinant viral vector in fully-grown plants. Transfected plants that overproduce the enzyme EPSPS in vegetative tissue (root, stem, and leaf) are resistant to Roundup® herbicide. The present invention provides a method for the production of plasmid-targeted EPSPS in plants via an RNA viral vector. A dual subgenomic promoter vector encoding the full-length EPSPS gene from *Nicotiana tabacum* (Class I EPSPS) is shown in plasmid pBS736. Systemic expression of the *Nicotiana tabacum* Class I EPSPS confers resistance to Roundup® herbicide in whole plants and tissue culture. FIG. 4 shows plasmid pBS736.

Example 3

*Arabidopsis thaliana* cDNA Library Construction in a Dual Subgenomic Promoter Vector.

*Arabidopsis thaliana* cDNA libraries obtained from the *Arabidopsis* Biological Resource Center (ABRC). The four libraries from ABRC were size-fractionated with inserts of 0.5–1 kb (CD4-13), 1–2 kb (CD4-14), 2–3 kb (CD4-15), and 3–6 kb (CD4-16). All libraries are of high quality and have been used by several dozen groups to isolate genes. The pBluescript® phagemids from the Lambda ZAP II vector were subjected to mass excision and the libraries were recovered as plasmids according to standard procedures.

Figure 5:
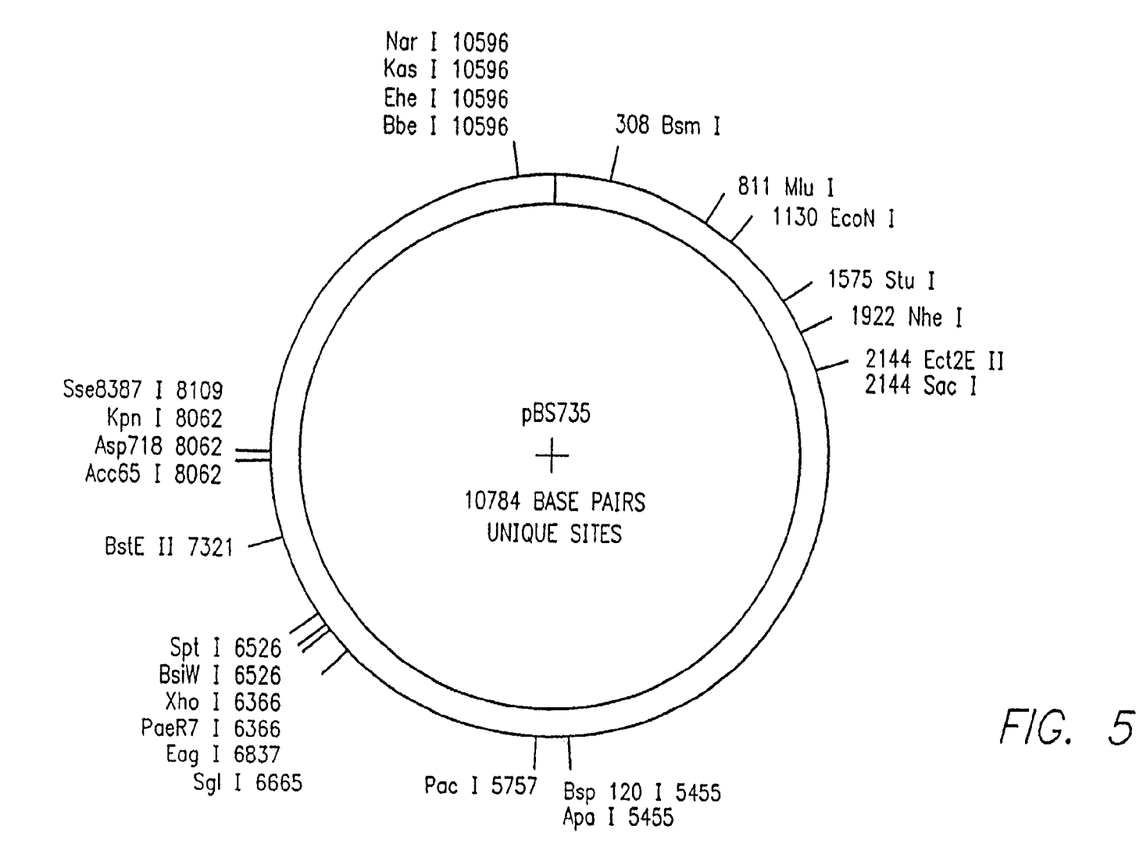
Figure 6:
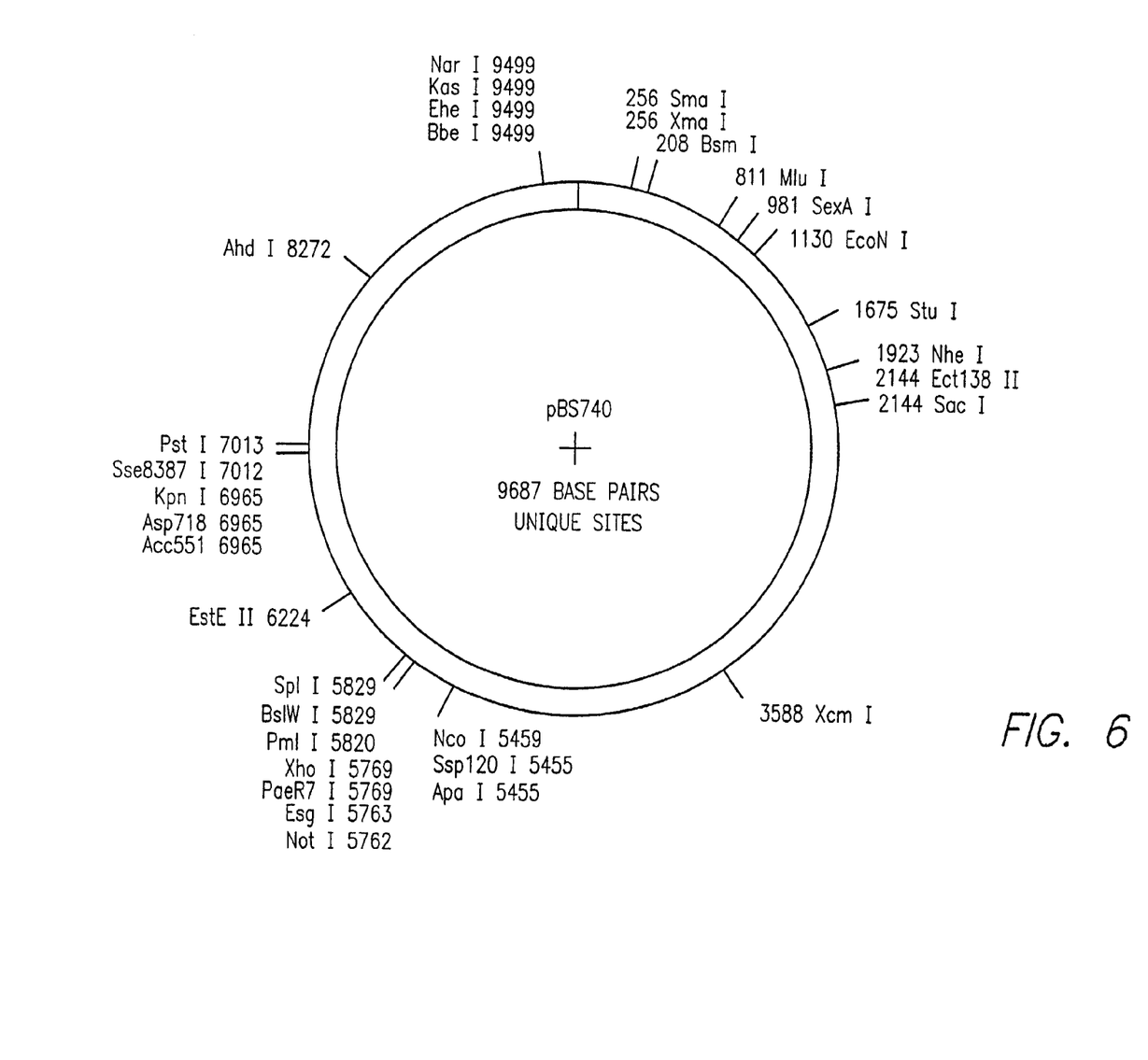

Alternatively, the cDNA inserts in the CD4-13 (Lambda ZAP II vector) were recovered by digestion with NotI. Digestion with NotI in most cases liberated the entire *Arabidopsis thaliana* cDNA insert because the original library was assembled with NotI adapters. NotI is an 8-base cutter that infrequently cleaves plant DNA. In order to insert the NotI fragments into a transcription plasmid, the pBS735 transcription plasmid (FIG. 5) was digested with PacI/XhoI and ligated to an adapter DNA sequence created from the oligonucleotides 5'-TCGAGCGGCCGCAT-3' (SEQ ID NO: 3) and 5'-GCGGCCGC-3' (SEQ ID NO: 4). The resulting plasmid pBS740 (FIG. 6) contains a unique NotI restriction site for bidirectional insertion of NotI fragments from the CD4-13 library. Recovered colonies were prepared from these for plasmid minipreps with a Qiagen BioRobot 9600®. The plasmid DNA preps performed on the BioRobot 9600® are done in 96-well format and yield transcription quality DNA. An *Arabidopsis* cDNA library was transformed into the plasmid and analyzed by agarose gel electrophoresis to identify clones with inserts. Clones with inserts are transcribed in vitro and inoculated onto *N. benthamiana* or *Arabidopsis thaliana*. Selected leaf disks from transfected plants are then taken for biochemical analysis. This cDNA library is screened in plant hosts in the presence of a herbicide or pathogen for resistance to herbicide, pests, or diseases. The nucleic acid sequence can be determined by further identifying the sequence of the nucleic acid insert in the recombinant viral nucleic acid library that results in growth changes of the plant hosts in the presence of a herbicide or pathogen. Such sequence may encode the target molecules of the herbicide or pathogen.

Example 4

Genomic DNA Library Construction in a Recombinant Viral Nucleic Acid Vector.

Genomic DNAs represented in BAC (bacterial artificial chromosome) or YAC (yeast artificial chromosome) libraries are obtained from the *Arabidopsis* Biological Resource Center (ABRC). The BAC/YAC DNAs are mechanically size-fractionated, ligated to adapters with cohesive ends, and shotgun-cloned into recombinant viral nucleic acid vectors. Alternatively, mechanically size-fractionated genomic DNAs are blunt-end ligated into a recombinant viral nucleic acid vector. Recovered colonies are prepared for plasmid minipreps with a Qiagen BioRobot 9600®. The plasmid DNA preps done on the BioRobot 9600® are assembled in 96-well format and yield transcription quality DNA. The recombinant viral nucleic acid/*Arabidopsis* genomic DNA library is analyzed by agarose gel electrophoresis (template quality control step) to identify clones with inserts. Clones with inserts are then transcribed in vitro and inoculated onto *N. benthamiana* and/or *Arabidopsis thaliana*. Selected leaf disks from transfected plants are then be taken for biochemical analysis.

Genomic DNA from *Arabidopsis* typically contains a gene every 2.5 kb (kilobases) on average. Genomic DNA fragments of 0.5 to 2.5 kb obtained by random shearing of DNA were shotgun assembled in a recombinant viral nucleic acid expression/knockout vector library. Given a genome size of *Arabidopsis* of approximately 120,000 kb, a random recombinant viral nucleic acid genomic DNA library would need to contain minimally 48,000 independent inserts of 2.5 kb in size to achieve 1× coverage of the *Arabidopsis* genome. Alternatively, a random recombinant viral nucleic acid genomic DNA library would need to contain minimally 240,000 independent inserts of 0.5 kb in size to achieve 1× coverage of the *Arabidopsis* genome. Assembling recombinant viral nucleic acid expression/knockout vector libraries from genomic DNA rather than cDNA has the potential to overcome known difficulties encountered when attempting to clone rare, low-abundance mRNA's in a cDNA library. A recombinant viral nucleic acid expression/knockout vector library made with genomic DNA would be especially useful as a gene silencing knockout library. In addition, the Dual Heterologous Subgenomic Promoter Expression System (DHSPES) expression/knockout vector library made with genomic DNA would be especially useful for expression of genes lacking introns. Furthermore, other plant species with moderate to small genomes (e.g. rose, approximately 80,000 kb) would be especially useful for recombinant viral nucleic acid expression/knockout vector libraries made with genomic DNA. A recombinant viral nucleic acid expression/knockout vector library can be made from existing BAC/YAC genomic DNA or from newly prepared genomic DNAs for any plant species. This genomic library is screened in plant hosts in the presence of a herbicide or pathogen for resistance to herbicide, pests, or diseases. The nucleic acid sequence can be determined by further identifying the sequence of the nucleic acid insert in the recombinant viral nucleic acid library that results in growth changes of the plant hosts in the presence of a herbicide or pathogen. Such sequence may encode the target molecules of the herbicide or pathogen.

Example 5

Construction of a *Nicotiana benthamiana* cDNA Library.

Vegetative *N. benthamiana* plants were harvested 3.3 weeks after sowing and sliced up into three groups of tissue: leaves, stems and roots. Each group of tissue was flash frozen in liquid nitrogen and total RNA was isolated from each group separately using the following hot borate method. Frozen tissue was ground to a fine powder with a pre-chilled mortar and pestle, and then further homogenized in pre-chilled glass tissue grinder. Immediately thereafter, 2.5 ml/g tissue hot (~82° C.) XT Buffer (0.2 M borate decahydrate, 30 mM EGTA, 1% (w/v) SDS. Adjusted pH to 9.0 with 5 N NaOH, treated with 0.1% DEPC and autoclaved. Before use, added 1% deoxycholate (sodium salt), 10 mM dithiothreitol, 15 Nonidet P-40 (NP-40) and 2% (w/v) polyvinylpyrrilidone, MW 40,000 (PVP-40)) was added to the ground tissue. The tissue was homogenized 1–2 minutes and quickly decanted to a pre-chilled Oak Ridge centrifuge tube containing 105 μl of 20 mg/ml proteinase K in DEPC treated water. The tissue grinder was rinsed with an additional 1 ml hot XT Buffer per g tissue, which was then added to rest of the homogenate. The homogenate was incubated at 42° C. at 100 rpm for 1.5 h. 2 M KCl was added to the homogenate to a final concentration of 160 mM, and the mixture was incubated on ice for 1 h to precipitate out proteins. The homogenate was centrifuged at 12,000×g for 20 min at 4° C., and the supernatant was filtered through sterile miracloth into a clean 50 ml Oak Ridge centrifuge tube. 8 M LiCl was added to a final concentration of 2 M LiCl and incubated on ice overnight. Precipitated RNA was collected by centrifugation at 12,000×g for 20 min at 4° C. The pellet was washed three times in 3–5 ml 4° C. 2 M LiCl. Each time the pellet was resuspended with a glass rod and then spun at 12,000×g for 20 min at 4° C. The RNA pellet was suspended in 2 ml 10 mM Tris-HCl (pH 7.5), and purified from insoluble cellular components by spinning at 12,000×g for 20 min at 4° C. The RNA containing supernatant was transferred to a 15 ml Corex tube and precipitated overnight at −20° C. with 2.5 volumes of 100% ethanol. The RNA was pelleted by centrifugation at 9,800×g for 30 min at 4° C. The RNA pellet was washed in 1–2 ml cold 70° C. ethanol and centrifuged at 9,800×g for 5 min at 4° C. Residual ethanol was removed from the RNA pellet under vacuum, and the RNA was resuspended in 200 μl DEPC treated dd-water and transferred to a 1.5 ml microfuge tube. The Corex tube was rinsed in 100 μl DEPC-treated dd-water, which was then added to the rest of the RNA. The RNA was then precipitated with 1/10 volume of 3 M sodium acetate, pH 6.0 and 2.5 volumes of cold 100% ethanol at −20° C. for 1–2 h. The tube was centrifuged for 20 min at 16,000×g, and the RNA pellet washed with cold 70% ethanol, and centrifuged for 5 min at 16,000×g. After drying the pellet under vacuum, the RNA was resuspended in DEPC-treated water. This is the total RNA.

Messenger RNA was purified from total RNA using an Poly(A)Pure kit (Ambion, Austin Tex.), following the manufacturer's instructions. A reverse transcription reaction was used to synthesize cDNA from the mRNA template, using either the Stratagene (La Jolla, Calif.) or Gibco BRL (Gaithersburg, Md.) cDNA cloning kits. For the Stratagene library, the cDNAs were subcloned into bacteriophage at EcoR1/XhoI site by ligating the arms using the Gigapack III Gold kit (Stratagene, La Jolla, Calif.), following the manufacturer's instructions. For the Gibco BRL library, the cDNAs were subcloned into a tobamoviral vector that contained a fusion of TMV-U1 and TMV-U5 at the NotI/XhoI sites. This cDNA library is screened in plant hosts in the presence of a herbicide or pathogen for resistance to herbicide, pests, or diseases. The nucleic acid sequence can be determined by further identifying the sequence of the nucleic acid insert in the recombinant viral nucleic acid library that results in growth changes of the plant hosts in the presence of a herbicide or pathogen. Such sequence may encode the target molecules of the herbicide or pathogen.

Example 6

Cytoplasmic Inhibition of 5-enolpyruvylshikimate-3-phosphate synthase (EPSPS) Genes in Plants Blocks aromatic amino acid biosynthesis.

Cytoplasmic inhibition of 5-enolpyruvylshikimate-3-phosphate synthase (EPSPS) genes in plants blocks aromatic amino acid biosynthesis and causes a systemic bleaching phenotype similar to Roundup® herbicide. See also della-Cioppa, et al., "Genetic Engineering of herbicide resistance in plants," *Frontiers of Chemistry: Biotechnology*, Chemical Abstract Service, ACS, Columbus, Ohio, pp. 665–70 (1989).

Figure 7:
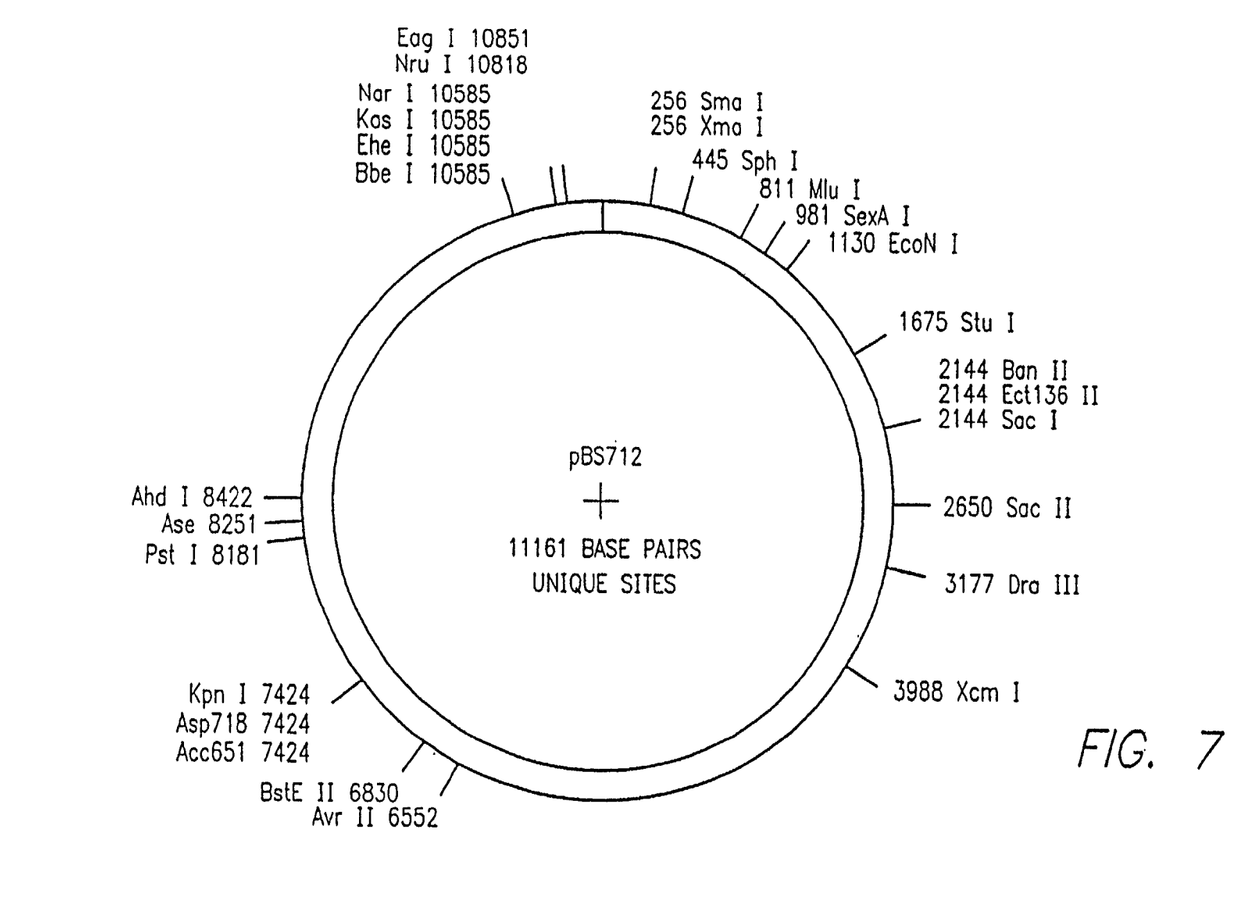

A dual subgenomic promoter vector encoding 1097 base pairs of an antisense EPSPS gene from *Nicotiana tabacum* (Class I EPSPS) is shown in plasmid pBS712. FIG. 7 shows plasmid pBS712. Systemic expression of the *Nicotiana tabacum* Class I EPSPS gene in the antisense orientation causes a systemic bleaching phenotype similar to Roundup® herbicide. This example shows that when the targets of an herbicide or pathogen are unknown or less defined, a library of sequence variants expressed in plant hosts in an antisense orientation may be employed to determine the targets of an herbicide or pathogen. More specifically, if the endogenous target gene is turned off by the antisense molecules, the growth of plant hosts is inhibited even in the absence of an herbicide or pathogen. Essentially, the antisensing molecules act as herbicides or pathogens in affecting plant growth. The nucleic acid sequence can be determined by further identifying the sequence of the nucleic acid insert in the recombinant viral nucleic acid library that results in growth inhibition of the plant hosts. Such sequence may be used to screen for resistance to herbicides or pathogens in a sense orientation.

Although the foregoing invention has been described in some detail by way of illustration and example for purposes of clarity of understanding, it will be obvious that certain changes and modifications may be practiced within the scope of the appended claims.

All publications, patents, patent applications are herein incorporated by reference in their entirety to the same extent as if each individual publication, patent, or patent application was specifically and individually indicated to be incorporated by reference in its entirety.

What is claimed is:

1. A method for conferring herbicide, pest, or disease resistance in a plant host comprising the steps of:
    (a) constructing a plant viral nucleic acid library comprising a plurality of plant viral nucleic acid sequences capable of being transcribed in a plant host;
    (b) transiently expressing the plant viral nucleic acid library in a plant host;
    (c) screening for nucleic acid sequences that confer resistance in the presence of an herbicide or a pathogen; and
    (d) repeating steps (a)–(c), if necessary, until at least one sequence in the plant viral nucleic acid library confers resistance to said plant host.

2. The method according to claim 1, wherein said plurality of plant viral nucleic acid sequences is derived from an RNA plant virus.

3. The method according to claim 1, wherein said plurality of plant viral nucleic acid sequences is derived from a single-stranded, plus sense RNA plant virus.

4. The method according to claim 1, wherein at least one of said plant viral nucleic acid sequences encodes an antimicrobial protein.

5. The method according to claim 1, wherein at least one of said plurality of plant viral nucleic acid sequences encodes an enzyme.

6. The method according to claim 1, wherein at least one of said plurality of plant viral nucleic acid sequences further comprises a promoter sequence operably linked to said nucleic acid sequence.

7. The method of claim 1, wherein at least one of said plurality of plant viral nucleic acid sequences is a nucleic acid sequence generated via in vitro mutagenesis, recombination, or a combination of the foregoing.

* * * * *